(12) United States Patent
Jouni et al.

(10) Patent No.: US 9,072,314 B2
(45) Date of Patent: Jul. 7, 2015

(54) CAROTENOID-CONTAINING COMPOSITIONS AND METHODS

(75) Inventors: Zeina Jouni, Battle Creek, MI (US); Zeina Makhoul, Tuscon, AZ (US)

(73) Assignee: Mead Johnson Nutrition Company, Glenview, IL (US)

( * ) Notice: Subject to any disclaimer, the term of this patent is extended or adjusted under 35 U.S.C. 154(b) by 0 days.

(21) Appl. No.: 13/486,760

(22) Filed: Jun. 1, 2012

(65) Prior Publication Data

US 2012/0238522 A1    Sep. 20, 2012

Related U.S. Application Data

(62) Division of application No. 12/206,838, filed on Sep. 9, 2008, now abandoned.

(60) Provisional application No. 60/986,029, filed on Nov. 7, 2007.

(51) Int. Cl.
| | |
|---|---|
| A61K 31/702 | (2006.01) |
| A61K 31/716 | (2006.01) |
| A61P 31/04 | (2006.01) |
| A23L 1/275 | (2006.01) |
| A23L 1/29 | (2006.01) |
| A23L 1/30 | (2006.01) |
| A23L 1/308 | (2006.01) |

(52) U.S. Cl.
CPC .............. *A23L 1/2753* (2013.01); *A23L 1/296* (2013.01); *A23L 1/30* (2013.01); *A23L 1/3088* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,788,468 | A | 1/1974 | Gainer |
| 3,975,519 | A | 8/1976 | Gainer |
| 4,046,880 | A | 9/1977 | Gainer |
| 5,234,702 | A | 8/1993 | Katz et al. |
| 5,602,103 | A | 2/1997 | Sugiura et al. |
| 5,602,109 | A | 2/1997 | Masor et al. |
| 5,635,199 | A | 6/1997 | Trimbo et al. |
| 5,854,015 | A | 12/1998 | Garnett et al. |
| 6,261,598 | B1 | 7/2001 | Runge et al. |
| 6,262,316 | B1 | 7/2001 | Wadstrom et al. |
| 6,265,450 | B1 | 7/2001 | Asami et al. |
| 6,565,891 | B1 | 5/2003 | Chandra |
| 6,617,305 | B1 | 9/2003 | Peters et al. |
| 6,727,373 | B2 | 4/2004 | Bijl et al. |
| 6,914,073 | B2 | 7/2005 | Boulos et al. |
| 6,923,967 | B1 | 8/2005 | Lignell |
| 7,090,879 | B2 | 8/2006 | Albrecht et al. |
| 2003/0165596 | A1 | 9/2003 | Lystrup et al. |
| 2003/0175364 | A1 | 9/2003 | Newman et al. |
| 2003/0206972 | A1 | 11/2003 | Babish et al. |
| 2003/0228392 | A1 | 12/2003 | Zimmer |
| 2004/0081628 | A1 | 4/2004 | Gierhart et al. |
| 2004/0191365 | A1 | 9/2004 | Leuenberger |
| 2005/0031736 | A1 | 2/2005 | Nguyen et al. |
| 2005/0058672 | A1 | 3/2005 | Gupta |
| 2005/0069505 | A1 | 3/2005 | Breton et al. |
| 2005/0123603 | A1 | 6/2005 | Dalland et al. |
| 2005/0255202 | A1 | 11/2005 | Dalziel et al. |
| 2006/0058269 | A1 | 3/2006 | Lockwood et al. |
| 2006/0106115 | A1 | 5/2006 | Yamaguchi |
| 2007/0077308 | A1 | 4/2007 | Giner |
| 2007/0207132 | A1 | 9/2007 | Speelmans et al. |

FOREIGN PATENT DOCUMENTS

| | | |
|---|---|---|
| EP | 0115620 | 11/1987 |
| EP | 0961552 | 6/2004 |
| EP | 1121106 | 6/2004 |
| EP | 0774251 | 7/2004 |
| EP | 1418822 | 3/2005 |
| EP | 1478329 | 5/2006 |
| JP | 2404356 | 10/1997 |
| JP | 1198972 | 4/1999 |
| JP | 3335360 | 8/2002 |
| JP | 2004035510 | 2/2004 |
| JP | 2004059518 | 2/2004 |
| JP | 2005225842 | 8/2005 |
| WO | 9837874 | 9/1998 |
| WO | 0023064 | 4/2000 |
| WO | 0137781 | 5/2001 |
| WO | 0230419 | 4/2002 |
| WO | 0317785 | 3/2003 |
| WO | 03070203 | 8/2003 |

(Continued)

OTHER PUBLICATIONS

Goodman, K. et al., Journal of Pediatric Gastroenterology & Nutrition, "Nutritional Factors and Helicobacter pylori Infection in Colombian Children", 1997, vol. 25, No. 5, pp. 507-515.*

Liu, B. H. et al., International Immunopharmacology, "Effect of total secondary carotenoids extracts from *Chlorococcum* sp. on *Helicobacter pylori*-infected BALB/c mice", 2003, vol. 3, pp. 979-986.*

Ziegler, Ekhard et al., Journal of Pediatric Gastroenterology and Nutrition, "Term Infants Fed Formula Supplemented with Selected Blends of Prebiotics Grow Normally and Have Soft Stools Similar to Those Reported for Breast-fed Infants", Mar. 2007, vol. 44, No. 3, pp. 359-364.*

Centers for Disease Control and Prevention, "*Helicobacter pylori*: Fact Sheet for Health Care Providers", Jul. 1998, pp. 1-4.*

(Continued)

*Primary Examiner* — Shaojia Anna Jiang
*Assistant Examiner* — Bahar Craigo
(74) *Attorney, Agent, or Firm* — Patterson Intellectual Property Law, P.C.; James R. Cartiglia; Tiffany N. Palmer

(57) ABSTRACT

The present invention is directed to carotenoid compositions and methods for inhibiting the growth of pathogenic bacteria or for preventing or treating bacterial infections in subjects by administration of an effective amount of astaxanthin and beta-carotene.

8 Claims, No Drawings

(56) References Cited

FOREIGN PATENT DOCUMENTS

| | | |
|---|---|---|
| WO | 2005102356 | 11/2005 |
| WO | 2005110122 | 11/2005 |

OTHER PUBLICATIONS

Crowe, S. E., UpToDatee®, "Patient information: *Helicobacter pylori* infection and treatment (Beyond the Basics)", pp. 1-7, Literature review current through Sept 2014; Topic last updated Aug. 2013.*

Myllyluoma, E. et al., Alimentary Pharmacology & Therapeutics, "Probiotic supplementation improves tolerance to *Helicobacter pylori* eradication therapy—a placebo-controlled, double-blind randomized pilot study", 2005, vol. 21, pp. 1263-1272.*

"Prevent", WordNet Search 3.1, last accessed Aug. 28, 2014; also available at http://wordnetweb.princeton.edu/.*

Hussein, G., et al., "Antihypertensive Potential and Mechanism of Action of Astaxanthin: III. Antioxidant and Histopathological Effects in Spontaneously Hypertensive Rats," Biol. Pharm. Bull. 29(4) 684-688 (2006).

Kato, S., et al., "Antibiotic Resistance of *Helicobacter pylori* Strains in Japanese Children," J. Clin. Microbiology, Feb. 2002 vol. 40(2), p. 649-653.

Megraud, F., "*H pylori* Antibiotic Resistance: Prevalence, Importance, and Advances in Testing," Gut 2004; 53:1374-1384.

Naito, Y., et al., "Prevention of diabetic nephropathy by treatment with astaxanthin in diabetic db/db mice," BioFactors 20 (2004) 49-59.

Obgami, K., et al., "Effects of Astaxanthin on Lipopolysaccharide-Induced Inflammation In Vitro and In Vivo," IOVS, Jun. 2003, vol. 44, No. 6, p. 2694-2701.

Solnick, J.V., et al., "Natural Acquisition of *Helecobacter pylori* Infection in Newborn Rhesus Macaques," J. Clinical Microbiology, Dec. 2003, vol. 41 (12), p. 5511-5516.

Wang, X., et al., "Astaxanthin-Rich Algal Meal and Vitamin C Inhibit *Helicobacter phylori* Infection in BALB/cA Mice," Antimicrobial Agents and Chemotherapy, Sep. 2000, vol. 44(9), p. 2452-2457.

Greer, F.R. et al., "Optimizing Bone Health and Calcium Intakes of Infants, Children, and Adolescents," Pediatrics vol. 117, No. 2 (2006) p. 578-585.

Martinez, F.D., "Viruses and Atopic Sensitization in the First Years of Life," Amer J of Respir and Critical Care Med, vol. 162 (2000) p. 595-599.

Pawley, N., et al., "Prenatal and infant predictors of bone health: the influence of vitamin D1-4," Am J Clin Nutr 2004:80(suppl: 1748S-51S.

* cited by examiner

CAROTENOID-CONTAINING COMPOSITIONS AND METHODS

CROSS-REFERENCE TO RELATED PATENT APPLICATIONS

This application is a divisional application which claims priority to commonly assigned U.S. patent application Ser. No. 12/206,838, filed Sep. 9, 2008, which claims priority to U.S. Provisional Application No. 60/986,029, filed Nov. 7, 2007, the disclosures of which are incorporated herein by reference in their entirety.

BACKGROUND OF THE INVENTION (1) Field of the Invention

The present invention relates generally to carotenoid-containing compositions, methods for inhibiting the growth of pathogenic bacteria, and methods for preventing or treating a bacterial infection in a subject via the administration of carotenoids.

(2) Description of the Related Art

Approximately two-thirds of the world's population is infected with Helicobacter pylori bacteria. Many people that are infected with the bacteria never suffer any symptoms related to the infection. In some cases, however, H. pylori infection can cause chronic active, chronic persistent, or atrophic gastritis. Infection with H. pylori also causes duodenal and gastric ulcers. In fact, H. pylori causes more than 90% of duodenal ulcers and 80% of gastric ulcers. The infection has additionally been associated with dyspepsia, iron-deficient anemia, and gastric malignancy. Further, approximately 15% of infected individuals will at some time develop peptic ulcer disease or gastric adenocarcinoma, which is the second most common cause of cancer deaths worldwide. Solnick, et al., *Natural Acquisition of Helicobacter pylori Infection in Newborn Rhesus Macaques*, J. Clin. Microbio. 41(12): 5511-5516 (2003).

Helicobacter pylori, which was previously known as Campylobacter pylori, is a gram-negative, spiral-shaped bacterium. It protects itself from the harsh acidic environment of the stomach by covering itself with the mucus of the stomach. Once covered, it is able to fight any stomach acid that does reach it with urease, an enzyme it possesses. Once nestled within the stomach mucus, H. pylori is able to penetrate the protective lining of the stomach, induce inflammatory cytokines, and cause gastric inflammation.

It is not currently known how H. pylori is transmitted or why some people become symptomatic while others do not. The bacteria are most likely spread from person to person through fecal-oral or oral-oral routes. Contaminated water or food sources may also contribute to the transmission of the bacteria.

The avoidance of H. pylori infection in infants and children is particularly important, as the incidence of H. pylori infection is greatest in childhood, particularly in developing countries where infection rates can be as high as 50% by age 5 years. Precise estimates of the age of acquisition of the infection are difficult to obtain because most children that are infected are asymptomatic. Even without symptoms, however, the infection can develop into more dangerous conditions such as antral gastritis, the most common manifestation in children. In addition, if an individual becomes infected with H. pylori during childhood, the infection may remain in his system throughout the course of his life, potentially leading to other diseases in adulthood.

Treatment for H. pylori infection currently consists of 10 days to 2 weeks of antibiotic treatment, such as with amoxicillin, tetracycline, metronidazole, or clarithromycin, plus either ranitidine bismuth citrate, bismuth subsalicylate, or a proton pump inhibitor. The disadvantage to widespread antibiotic treatment is the development of antibiotic resistance. The H. pylori infection has previously been shown to be resistant to several antibiotic treatments, contributing to treatment failure in a number of cases. F Mégraud, *H pylori Antibiotic Resistance: Prevalence, Importance, and Advances in Testing*, Gut 53: 1374-1384 (2004). In a particular study, 29% of the H. pylori strains tested were resistant to clarithromycin, 24% to metronidazole, and 10% were resistant to both clarithromycin and metronidazole. Kato, et al., *Antibiotic Resistance of Helicobacter pylori Strains in Japanese Children*, J. Clin. Microbio. 40(2): 649-653 (2002). Thus, infected individuals cannot be assured that antibiotic treatment will be effective.

Therefore, a need remains for a method for preventing or treating H. pylori infection in subjects. It would also be beneficial to provide a method for achieving such prevention or treatment through the use of compositions other than traditional antibiotics.

SUMMARY OF THE INVENTION

Briefly, therefore, the present invention is directed to a nutritional composition comprising astaxanthin, beta-carotene, galacto-oligosaccharide, and polydextrose.

In another embodiment, the invention is directed to a method for inhibiting the growth of pathogenic bacteria in a subject comprising administering to the subject an effective amount of astaxanthin and beta-carotene.

The invention is additionally directed to a method for inhibiting the growth of H. pylori in an infant comprising administering to the infant an infant formula containing an effective amount of astaxanthin and beta-carotene.

In other embodiments, the invention is directed to a method for preventing or treating a bacterial infection or preventing obesity in a subject comprising administering to the subject a nutritional composition comprising astaxanthin, beta-carotene, galacto-oligosaccharide, and polydextrose.

DETAILED DESCRIPTION OF THE PREFERRED EMBODIMENTS

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Carotenoids are a related group of greater than 600 natural compounds, irrespective of geometric and stereoisomers, with demonstrated antioxidant efficacy. The carotenoids are broadly divided into "carotenes," or non-oxygen substituted hydrocarbon carotenoids, and "xanthophylls," oxygen-substituted carotenoids. Between 500 and 600 carotenoids have been identified, of which only about 24 occur in human foodstuffs. The major carotenoids found in foods are α-carotene, β-carotene, lycopene, lutein, zeaxanthin, and β-cryptoxanthin. They are present in foods such as carrots, pumpkins, sweet potatoes, tomatoes, and other deep green, yellow, orange, red fruits and vegetables. Most carotenoids occur in nature predominantly in the all-trans form. Three of these carotenoids, α-carotene, β-carotene and β-cryptoxanthin, can be converted into retinol and are therefore considered provitamin A carotenoids. Lycopene, lutein and zeaxanthin do not have a vitamin A function and are referred to as nonprovitamin A carotenoids.

An important feature of carotenoids is a centrally located, extended conjugated double-bond system, which is responsible for the chemical reactivity, light-absorbing properties, and, thus, the color of carotenoids. Potential biological function is determined by the chemical structure of carotenoids. The alternating single and double bond of the polyene backbone of carotenoids allow them to absorb excess energy from other molecules, which accounts for their antioxidant properties. They perform their antioxidant function by either quenching singlet oxygen and/or blocking free radical-mediated reactions. The polarity of the specific end groups of carotenoids accounts for the differences in how they interact with biological membranes. Carotenoids are associated with lipid portions of human tissues, cells, and membranes and bind to hydrophobic surfaces because they are lipophilic. In addition, carotenoids are easily isomerized and oxidized due to their high unsaturation and hence may lose biological activity after processing and storage.

In recent years, carotenoids have received the interest of researchers from diverse fields including food science, pharmacy, biochemistry and nutrition because of their wide spectrum of biological functions such as provitamin A, antioxidant, immuno-enhancement, and prevention of degenerative diseases.

For example, see U.S. Pat. No. 7,090,879 to Albrecht, et al., U.S. Pat. No. 6,268,450 to Asami, et al., U.S. Pat. No. 6,727,373 to Bijl, et al., U.S. Patent App. Pub. No. 2003/0175364 to Newman, et al., or U.S. Patent App. Pub. No. 2006/0068019 to Dalziel, et al.

The technical problem to be solved by the present invention is to provide novel carotenoid nutritional compositions that are useful in inhibiting the growth of pathogenic bacteria and/or preventing or treating bacterial infections in subjects. Thus, in an embodiment, the present invention is directed to a nutritional composition comprising astaxanthin, beta-carotene, galacto-oligosaccharide, and polydextrose. The present invention is also directed, in an embodiment, to a method for inhibiting the growth of pathogenic bacteria or for preventing or treating bacterial infections in subjects by administering to them an effective amount of astaxanthin and beta-carotene.

Astaxanthin is a fat-soluble, oxygenated pigment which is classified as a xanthophyll and is a member of the carotenoid family. It has a unique molecular structure that gives it powerful antioxidant function. It can be extracted from salmon, microalgae, and Pfaffia, a yeast. Current research shows that due to astaxanthin's potent antioxidant activity, it may be beneficial in cardiovascular, immune, anti-inflammatory, and neurodegenerative diseases. Specifically, its varied actions include: inhibition of lipid peroxidation at the cell level; crossing the blood-brain barrier, effecting treatment of ocular and neurodegenerative diseases such as glaucoma and Alzheimer's; entrapment of free radicals by adding them to its long, double-bonded chain rather than donating an electron; stabilization of the cell membrane via its polar end groups spanning the cell membrane and increasing its rigidity and mechanical strength; neutralization of singlet and triplet oxygen (de-charges) generated by UVA and UVB radiation and other sources; binding to a lipoprotein, an efficient transport vehicle, making it more bioavailable; increase of immune system function including heightened production of antibody-secreting cells and Interleukin 2 and suppression of interferon-gamma; inhibition of reactive oxygen species that cause inflammation; enhancing of the antioxidant actions of Vitamin E and Vitamin C; and encouraging the release of Vitamin A from the liver when needed.

Astaxanthin provides significantly more antioxidant capacity than other carotenoids and antioxidants such as beta-carotene and Vitamin E. In fact, Astaxanthin has 100-500 times the antioxidant capacity of Vitamin E and 10 times the antioxidant capacity of beta-carotene. Many laboratory studies also indicate astaxanthin is a stronger antioxidant than lutein, lycopene and tocotrienols. Astaxanthin is often added to food products or nutritional supplements for its antioxidant effects.

The structure of astaxanthin is shown below:

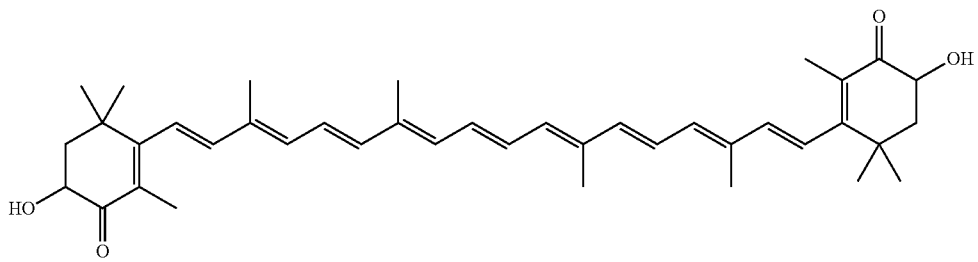 [SMILES: CC1=C(/C=C/C(C)=C/C=C/C(C)=C/C=C/C=C(C)/C=C/C=C(C)/C=C/C2=C(C)C(=O)C(O)CC2(C)C)C(C)(C)CC(O)C1=O]

In an embodiment of the invention, the effective amount of astaxanthin is within the range of about 0.01 mg and about 10 mg per kg body weight per day. In another embodiment of the invention, the effective amount of astaxanthin is within the range of about 0.1 mg and about 5 mg per kg body weight per day. In a particular embodiment of the invention, the effective amount of astaxanthin is about 1 mg per kg body weight per day.

Like astaxanthin, beta-carotene is a carotenoid. Beta-carotene is the most common of the carotenes and can be found in yellow, orange, and green leafy fruits and vegetables. It is unclear whether beta-carotene has any biological function for humans other than as a precursor for vitamin A. There is some evidence that beta-carotene may play a beneficial role in human nutrition beyond its provitamin A function. Beta-carotene has antioxidant activity, at least in vitro, and it may enhance intercellular communication and may have immunomodulatory and anticarcinogenic activities in certain circumstances.

The structure of beta-carotene is set forth below:

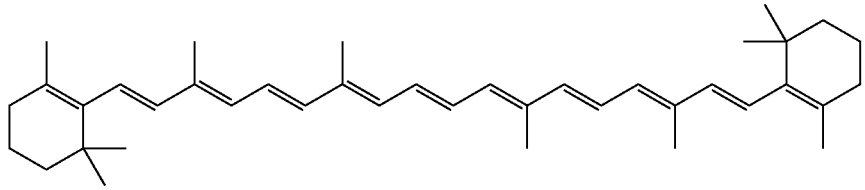 [SMILES: CC1=C(/C=C/C(C)=C/C=C/C(C)=C/C=C/C=C(C)/C=C/C=C(C)/C=C/C2=C(C)CCCC2(C)C)C(C)(C)CCC1]

In an embodiment of the invention, the effective amount of beta-carotene is within the range of about 0.01 mg and about 10 mg per kg body weight per day. In another embodiment of the invention, the effective amount of beta-carotene is within the range of about 0.1 mg and about 5 mg per kg body weight per day. In a particular embodiment of the invention, the effective amount of beta-carotene is about 1 mg per kg body weight per day.

As used in the present invention, the source of either astaxanthin or beta-carotene can be any source known in the art such as plant material, seafood, and/or single cell. In certain embodiments, either of astaxanthin or beta-carotene may be in raw form or may be chemically manipulated. In a particular embodiment, either of astaxanthin or beta-carotene may be genetically modified organisms.

As noted, the present invention is directed, in certain embodiments, methods for inhibiting the growth of pathogenic bacteria or for preventing or treating bacterial infections in subjects by administering to them an effective amount of astaxanthin and beta-carotene. The pathogenic bacteria which experience growth inhibition as a result of the invention may be any pathogenic bacteria known in the art. In a particular embodiment, the pathogenic bacteria is *H. pylori*. Likewise, the bacterial infection of the invention may be any known in the art, but in a particular embodiment, is *H. pylori* infection.

In an embodiment, the astaxanthin and beta carotene may be administered in the form of a nutritional composition, infant formula, human milk supplement, or children's nutritional product. As used herein, the term "infant formula" means a composition that satisfies the nutrient requirements of an infant by being a substitute for human milk. Thus, the method of the invention is useful in preventing or treating bacterial infections in human infants, children, or adults.

If the astaxanthin and beta-carotene are administered via an infant formula, the infant formula may be nutritionally complete and contain suitable types and amounts of lipid, carbohydrate, protein, vitamins and minerals. The amount of lipid or fat typically can vary from about 3 to about 7 g/100 kcal. The amount of protein typically can vary from about 1 to about 5 g/100 kcal. The amount of carbohydrate typically can vary from about 8 to about 12 g/100 kcal. Protein sources can be any used in the art, e.g., nonfat milk, whey protein, casein, soy protein, hydrolyzed protein, and/or amino acids. Carbohydrate sources can be any used in the art, e.g., lactose, glucose, corn syrup solids, maltodextrins, sucrose, starch, and/or rice syrup solids. Lipid sources can be any used in the art, e.g., vegetable oils such as palm oil, canola oil, corn oil, soybean oil, palmolein, coconut oil, medium chain triglyceride oil, high oleic sunflower oil, and/or high oleic safflower oil.

Conveniently, commercially available nutritional compositions, infant formulas, human milk supplements, or children's nutritional products can be used. For example, Enfalac, Enfamil®, Enfamil® Premature Formula, Enfamil® with Iron, Enfamil® LIPIL®, Lactofree®, Nutramigen®, Pregestimil®, and ProSobee® (available from Mead Johnson & Company, Evansville, Ind., U.S.A.) may be supplemented with suitable levels of astaxanthin and beta-carotene and used in practice of the invention.

If the astaxanthin and beta-carotene are administered in an infant formula, the amounts of each carotenoid in the formula may be up to about 40 nmol/g fat. In another embodiment, the amounts of each carotenoid in the formula may be within the range of about 2 nmol/g and about 35 nmol/g fat. In a particular embodiment, the amounts of each carotenoid in the formula may be within the range of about 5 nmol/g and about 30 nmol/g fat.

The total carotenoid blend may comprise, in an embodiment, up to about 2000 mcg/L infant formula. In other embodiments, the total carotenoid blend may comprise from about 100 to about 1500 mcg/L infant formula. In yet another embodiment, the total carotenoid blend may comprise from about 200 to about 1200 mcg/L infant formula.

The individual carotenoids may be present in the infant formula in an amount of from about 50 to about 1150 mcg/L, about 75 to about 230 mcg/L, or about 100 to about 200 mcg/L.

In some embodiments of the invention, additional components may be administered in combination with astaxanthin and beta-carotene. These additional components may include probiotics, prebiotics, or long chain polyunsaturated fatty acids (LCPUFAs). The components may be administered separately from the astaxanthin and beta-carotene or may be included as part of a nutritional composition, infant formula, human milk supplement, or children's nutritional product that contains astaxanthin, beta-carotene, and one or more additional components.

The term "probiotic" means a microorganism that exerts beneficial effects on the health of the host. Any probiotic known in the art may be used, provided it is suitable for combination with the other components of the supplement. For example, the probiotic may be chosen from the group consisting of *Lactobacillus* and *Bifidobacterium*. Alternatively, the probiotic can be *Lactobacillus rhamnosus* GG.

The term "prebiotic", as used herein, means a non-digestible food ingredient that stimulates the growth and/or activity of probiotics. In this embodiment, any prebiotic known in the art may be used, provided it is suitable for combination with the other components of the supplement. In a particular embodiment, the prebiotic can be selected from the group consisting of fructo-oligosaccharide, gluco-oligosaccharide, galacto-oligosaccharide, inulin, isomalto-oligosaccharide, polydextrose, xylo-oligosaccharide, lactulose, and combinations thereof. In a particular embodiment, the prebiobic is a mixture of galacto-oligosaccharide and polydextrose.

In an embodiment, the total amount of prebiotics present in the nutritional composition may be from about 1.0 g/L to about 10.0 g/L of the composition. In another embodiment, the total amount of prebiotics present in the nutritional composition may be from about 2.0 g/L and about 8.0 g/L of the composition. In yet another embodiment, the total amount of prebiotics present in the nutritional composition may be about 4.0 g/L of the composition.

If galacto-oligosaccharide is used as a prebiotic, the amount of galacto-oligosaccharide in the nutritional composition may, in an embodiment, be within the range of from about 1.0 g/L to about 4.0 g/L. In another embodiment, the amount of galacto-oligosaccharide in the nutritional composition may be about 2.0 g/L. If polydextrose is used as a prebiotic, the amount of polydextrose in the nutritional composition may, in an embodiment, be within the range of from about 1.0 g/L to about 4.0 g/L. In another embodiment, the amount of polydextrose in the nutritional composition may be about 2.0 g/L. In a particular embodiment, galacto-oligosaccharide and polydextrose are supplemented into the nutritional composition in a total amount of about 4.0 g/L. In this embodiment, the amount of galacto-oligosaccharide may be about 2.0 g/L and the amount of polydextrose may be about 2.0 g/L.

While not wishing to be bound to this or any theory, it is believed that the administration of prebiotics and carotenoids may provide a synergistic effect. More specifically, it is believed that the prebiotic may alter the composition of the gut flora to provide a greater number of beneficial bacteria and fewer pathogenic bacteria, further contributing to the antimicrobial effect of the carotenoids in the present invention.

In yet another embodiment of the invention, LCPUFAs may be administered in combination with astaxanthin and beta-carotene. In this embodiment, the LCPUFAs may include docosahexaenoic acid (DHA), arachidonic acid (ARA), and/or eicosapentaenoic acid (EPA).

If administered as part of the present invention, the weight ratio of ARA:DHA may be from about 1:3 to about 9:1. In one embodiment of the present invention, this ratio is from about 1:2 to about 4:1. In yet another embodiment, the ratio is from about 2:3 to about 2:1. In one particular embodiment the ratio is about 2:1. In another particular embodiment of the invention, the ratio is about 1:1.5. In other embodiments, the ratio is about 1:1.3. In still other embodiments, the ratio is about 1:1.9. In a particular embodiment, the ratio is about 1.5:1. In a further embodiment, the ratio is about 1.47:1.

If administered as part of the present invention, the level of DHA may be within the range of about 0.0% and about 1.00% of fatty acids, by weight. In other embodiments, the level of DHA may be about 0.32% by weight. In some embodiments, the level of DHA may be about 0.33% by weight. In another embodiment, the level of DHA may be about 0.64% by weight. In another embodiment, the level of DHA may be about 0.67% by weight. In yet another embodiment, the level of DHA may be about 0.96% by weight. In a further embodiment, the level of DHA may be about 1.00% by weight.

If administered as part of the present invention, the level of ARA may be within the range of 0.0% and 0.67% of fatty acids, by weight. In another embodiment, the level of ARA may be about 0.67% by weight. In another embodiment, the level of ARA may be about 0.5% by weight. In yet another embodiment, the level of DHA may be within the range of about 0.47% and about 0.48% by weight.

If administered as part of the present invention, the amount of DHA may be from about 2 mg/100 kilocalories (kcal) to about 100 mg/100 kcal. In another embodiment, the amount of DHA may be from about 5 mg/100 kcal to about 75 mg/100 kcal. In yet another embodiment, the amount of DHA may be from about 15 mg/100 kcal to about 60 mg/100 kcal.

If administered as part of the present invention, the amount of ARA may be from about 4 mg/100 kilocalories (kcal) to about 100 mg/100 kcal. In another embodiment, the amount of ARA may be from about 10 mg/100 kcal to about 67 mg/100 kcal. In yet another embodiment, the amount of ARA may be from about 20 mg/100 kcal to about 50 mg/100 kcal. In a particular embodiment, the amount of ARA may be from about 25 mg/100 kcal to about 40 mg/100 kcal. In one embodiment, the amount of ARA is about 30 mg/100 kcal.

If administered as part of the present invention, the effective amount of DHA may be from about 3 mg per kg of body weight per day to about 150 mg per kg of body weight per day. In one embodiment of the invention, the amount is from about 6 mg per kg of body weight per day to about 100 mg per kg of body weight per day. In another embodiment the amount is from about 15 mg per kg of body weight per day to about 60 mg per kg of body weight per day.

If administered as part of the present invention, the effective amount of ARA may be from about 5 mg per kg of body weight per day to about 150 mg per kg of body weight per day. In one embodiment of this invention, the amount varies from about 10 mg per kg of body weight per day to about 120 mg per kg of body weight per day. In another embodiment, the amount varies from about 15 mg per kg of body weight per day to about 90 mg per kg of body weight per day. In yet another embodiment, the amount varies from about 20 mg per kg of body weight per day to about 60 mg per kg of body weight per day.

If the composition of the invention is supplemented with oils containing LCPUFAs, it may be accomplished using standard techniques known in the art. For example, an equivalent amount of an oil which is normally present in a composition, such as high oleic sunflower oil, may be replaced with the LCPUFAs.

If utilized, the source of the LCPUFAs can be any source known in the art such as marine oil, fish oil, single cell oil, egg yolk lipid, and/or brain lipid. The LCPUFAs can be in natural form or refined form.

In other embodiments of the invention, astaxanthin and beta-carotene may be combined and administered to a subject for the purpose of treating or preventing any of the following: reflux, spitting up, abdominal pain, bloating, vomiting, gastric inflammation, gastritis, ulcer formation, hypertension, dyslipidemia, Type I and II diabetes, insulin sensitivity, obesity, cardiovascular disease, cancer, atherosclerosis. In other embodiments, astaxanthin and beta-carotene can be combined and administered for the purpose of improving digestion or stool consistency, modulating antioxidant enzymes, decreasing cellular and tissue oxidative stress, shifting T-helper cell Types 1 to Th2 balance, and modulating immune function.

In some embodiments, the invention includes a method for improving weight management in a subject comprising administering to the subject an effective amount of astaxanthin and beta-carotene. In other embodiments, the invention includes a method for preventing or treating obesity in a subject comprising administering to the subject an effective amount of astaxanthin and beta-carotene. Obesity has been linked with an inflammation of adipose tissue. In some studies, inflammation has also been identified as an early characteristic of obesity. The combination of astaxanthin and beta-carotene, in addition to their antioxidant benefits, may contribute to a reduction in inflammation, thereby reducing or preventing the onset of obesity in the present invention.

In an embodiment, the invention is directed to the use of a combination of astaxanthin and beta-carotene in the manufacture of an ingestible composition for inhibiting the growth of pathogenic bacterial in a subject. In another embodiment, the invention is directed to the use of a combination of astaxanthin and beta-carotene in the manufacture of an ingestible composition for inhibiting the growth of *H. pylori* in an infant. In yet another embodiment, the invention is directed to the use of a combination of astaxanthin and beta-carotene in the manufacture of an ingestible composition for preventing or treating a bacterial infection in a subject. In still another embodiment, the invention is directed to the use of a combination of astaxanthin and beta-carotene in the manufacture of an ingestible composition for preventing obesity in a subject.

The invention, in an embodiment, is also directed to a combination of astaxanthin and beta-carotene for use in inhibiting the growth of pathogenic bacteria in a subject. The invention is also directed, in an embodiment, to a combination of astaxanthin and beta-carotene for use in inhibiting the growth of *H. pylori* in an infant. Additionally, the invention is directed, in an embodiment, to a combination of astaxanthin and beta-carotene for use in preventing or treating a bacterial infection in a subject.

All references cited in this specification, including without limitation, all papers, publications, patents, patent applications, presentations, texts, reports, manuscripts, brochures, books, internet postings, journal articles, and/or periodicals are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

What is claimed is:

1. A method for inhibiting the growth of *H. pylori* in an infant in which *H. pylori* is present, comprising administering to the infant a nutritional composition comprising a carbohydrate source, a lipid source, a protein source, beta-carotene in an amount of from about 50 mcg/L to about 1150 mcg/L, astaxanthin in an amount of from about 50 mcg/L to about 1150 mcg/L, polydextrose, galactooligosaccharide, and *Lactobacillus rhamnosus* GG.

2. The method of claim 1, wherein the nutritional composition comprises each of astaxanthin and beta-carotene in an amount within the range of from about 75 mcg/L to about 230 mcg/L.

3. The method of claim 2, wherein the nutritional composition comprises each of astaxanthin and beta-carotene in an amount within the range of from about 100 mcg/L to about 200 mcg/L.

4. The method of claim 1, wherein the nutritional composition comprises up to about 2000 mcg/L of the carotenoid blend.

5. The method of claim 1, wherein the nutritional composition comprises galacto-oligosaccharide in an amount in the range of from about 1.0 g/L to about 4.0 g/L.

6. The method of claim 1, wherein the nutritional composition comprises polydextrose in an amount in the range of from about 1.0 g/L to about 4.0 g/L.

7. The method of claim 1 wherein the nutritional composition is an infant formula.

8. The method of claim 1, wherein the nutritional composition further comprises, in addition to the lipid source, arachidonic acid and docosahexanoic acid having a weight ratio of from about 1:3 to about 9:1.

\* \* \* \* \*